United States Patent [19]

Moore

[11] Patent Number: Plant 6,548

[45] Date of Patent: Jan. 17, 1989

[54] HYBRID MINIATURE ROSE PLANT CV. MORPAPPLAY

[75] Inventor: Ralph S. Moore, Visalia, Calif.

[73] Assignee: Bear Creek Gardens, Inc., Medford, Oreg.

[21] Appl. No.: 48,446

[22] Filed: May 11, 1987

[51] Int. Cl.[4] ..... A01H 5/00

[52] U.S. Cl. ..... Plt./2

[58] Field of Search ..... Plt./2

*Primary Examiner*—Robert E. Bagwill

*Attorney, Agent, or Firm*—Synnestvedt & Lechner

[57] ABSTRACT

This invention relates to a new and distinct variety of hybrid miniature rose plant cv. morPapplay, primarily identified by its red and yellow buds and flowers and its prostrate habit of growth.

1 Drawing Sheet

The present invention relates to a new and distinct variety (cv. morPapplay) of rose plant of the hybrid miniature class. The plant is a hardy, outdoor seedling of the climbing or trailing type, with prostrate, spreading growth habit, cultivated for garden decoration and ground cover. It was first originated by Ralph S. Moore (a citizen of the U.S. residing at Visalia, County of Tulare, Calif.) under conditions of careful control and observation, and has as its seed parent the miniature climbing rose Papoose (unpatented) and as its pollen parent, the floribunda rose Playboy (unpatented).

The new rose cv. morPapplay is particularly distinguishable from other commercialized rose cultivars by the following combination of characteristics: its red and yellow buds and flowers, essentially as described and illustrated herein; its abundance of bloom, with flowers usually borne several to the stem in clusters; its slight apple blossom fragrance; its vigorous, spreading, and prostrate growth habit; and its small, semi-glossy matt foliage with pointed leaflets. Its buds and flowers are similar in form and size to Sheri Anne, U.S. Plant Pat. No. 3,826, but flatter when fully open.

The plant has a normal height of 8 to 10 inches with a spread of 5 feet or more, but can easily be maintained at lesser size by occasional trimming.

The plant grows and blooms satisfactorily outdoors in the garden, is good for growing in large pots or tubs, and provides excellent garden decoration when used as a ground cover or trained on a fence or trellis.

The plant holds its distinguishing characteristics through succeeding propagations by cuttings and budding.

The new variety cv. morPapplay may be distinguished from its seed parent Papoose (unpatented) by the following combination of characteristics: Whereas flower color of Papoose is white, the flower color of morPapplay is cardinal red with a yellow center on the inside surface of the petal and lemon yellow at the petal base, becoming light reddish yellow on the upper part of the outside petal surface. The bush size of Papoose is smaller, spreading approximately 3–4 feet in diameter, whereas the bush size of morPapplay is larger, spreading 5 feet or more. The bloom diameter is smaller in Papoose being about 1 inch in diameter, while the blooms of morPapplay are larger, approximately 2 inches in diameter. Whereas the petalage of Papoose is single, morPapplay has double petalage, averaging about 18 petals per flower.

The new variety may be distinguished from its pollen parent Playboy (unpatented) by the following combination of characteristics: Whereas the bush characteristic of Playboy is upright and is classified as a Floribunda, morPapplay is prostrate and is classified as a ground cover. The flowers of Playboy are single whereas those of morPapplay are double. Whereas the flowers of Playboy are larger and measure approximately 3.5 inches in diameter, those of morPapplay average only 2 inches in diameter.

The accompanying drawing illustrates the new variety in color as grown as Visalia, Calif., and shows the flowering thereof from bud to full bloom.

The descriptive matter which follows pertains to roses of the new variety grown outdoors at Visalia and also Somis, Calif., and is believed generally to apply to similar conditions of soil and climate elsewhere. Plants and flowers of the new variety grown in other locations may vary in slight detail according to the climatic, soil and cultural conditions under which the variety is grown.

Throughout this specification, color names beginning with a small letter signify that the name of that color as used in common speech is aptly descriptive. Color names beginning with a capital letter designate values based upon The Horticultural Colour Chart of the British Colour Council.

FLOWER

The new variety usually bears its flowers several to a stem in clusters or sprays of 5 to 10 flowers or more.

BUD

The peduncle is short, slender but sturdy, and erect. It has no prickles and few or no hairs and is medium to light green in color, sometimes tinted with bronze outdoors.

Before the calyx breaks, the bud is small for the class and long and pointed in form. There are few foliaceous appendages on the surface of the bud, with foliaceous parts extending beyond the tip of the bud and equal to one-half or less of its length. Bud color is medium green, occasionally tinted with bronze outdoors.

As the calyx breaks, bud color is usually red but may also show yellow.

The bud opens well in all weather.

BLOOM

The size of the bloom when fully open is small for the class, averaging about 2 inches (50 mm) in diameter.

Petalage is double, averaging about 18 petals arranged regularly, plus 2 or 3 small petaloids. Bloom form is high-centered at first, becoming cupped and then relatively flat, with petals rolled loosely outward and downward. Open flowers show stamens.

The petals are fairly thick, satiny on the inside and outside surfaces. Outside petals are broadly lanceolate (wedge-shaped) with rounded tips. Intermediate petals are broadly lanceolate with rounded tips. Inside petals are lanceolate with rounded tips.

The following paragraph describes the color values observed in a newly opened flower from a plant of the new variety grown outdoors in Visalia, Calif. in the Spring of 1985.

The outside surface of the outside petals is near Lemon Yellow 4/2 at the base, becoming light reddish yellow (red bleeds through from upper surface) on the top two-thirds of the petal. The inside surface of the outside petals is near Cardinal Red 822/2 or lighter in color, overlaid (veined) with darker, blackish red, giving the petal surface the overall appearance of being darker red (near Cardinal Red 822 or darker), the whole of the surface being underlaid with yellow. The base third of the inside surface of the inside petals is bright yellow, near Lemon Yellow 4/1 in color.

The outside and inside surfaces of the intermediate and inner petals are similar to the outside and inside surfaces, respectively, of the outside petals.

The general color effect of the bud and newly opened flowers is bright red and yellow bicolor, similar to Forty Niner, U.S. Plant Pat. No. 792 (expired). The general color effect of a flower three days open is similar to, but lighter than, the color effect of the newly opened flowers. The red color of the petals and flowers may be modified by blending and interaction of the red and yellow colors plus the darker, blackish veining.

Petals usually drop off cleanly. Flowers on garden plants grown in the spring of 1985 last from 4 to 5 days.

REPRODUCTIVE ORGANS

Stamens are arranged regularly about the pistils. Filaments vary in length, tending to be medium long, and are yellow in color. Most have well-formed, yellow anthers. Pollen is produced in small amount.

Pistils are average in number for the class. Styles are of varying length, tending to be quite short, and are bunched; style color is reddish. Ovaries are usually all enclosed in the calyx.

Plants of the variety grown at Visalia, Calif., do not see hips.

Sepals are permanent, spear-shaped and recurved.

Seed is not produced.

FOLIAGE

The compound leaves are leathery, semi-glossy to matte, and usually comprise 5 leaflets, sometimes 3 or 7, of small size for the class. Leaflets are broad and nearly oval in shape, with acute apices; their bases are usually rounded, but sometimes acute.

The color of the foliage is medium green; new growth is normal, medium green, often tinted reddish.

The rachis is of medium strength. Its upper side is grooved and has no prickles and few or no hairs; the underside may have several thorns (1 to 3) and has few or no tiny prickles or hairs.

Stipules are medium to long in length for the class, of medium to narrow width, and have short to medium-length points which usually turn out at an angle of about 45°.

GROWTH

Plants of the new variety are of dwarf habit, climbing or prostrate and trailing, and much branched. Plant growth is free and vigorous; internodes are short. Canes are slender and sturdy. The main stems are medium green in color. They bear several thorns of brownish color, straight and inclined downward. There are no prickles or hairs.

Branches are medium green in color; they bear several slender thorns. There are no prickles or hairs.

I claim:

1. A new and distinct variety of climbing miniature rose plant cv. morPapplay and the parts thereof, of hardy, compact, prostrate and trailing, much-branched habit; being particularly characterized by its abundance of flowers, usually borne in clusters of 5 to 10 or more; its buds and flowers of pleasing form, the petals being a blend of red and yellow shades, essentially red on their top surface and yellow on the lower surface; its vigorous growth; its moderately thorny shoots and main stems; its abundance of small, semi-glossy to matt foliage; and its ease of propagation by cuttings or budding, substantially as described and illustrated herein.

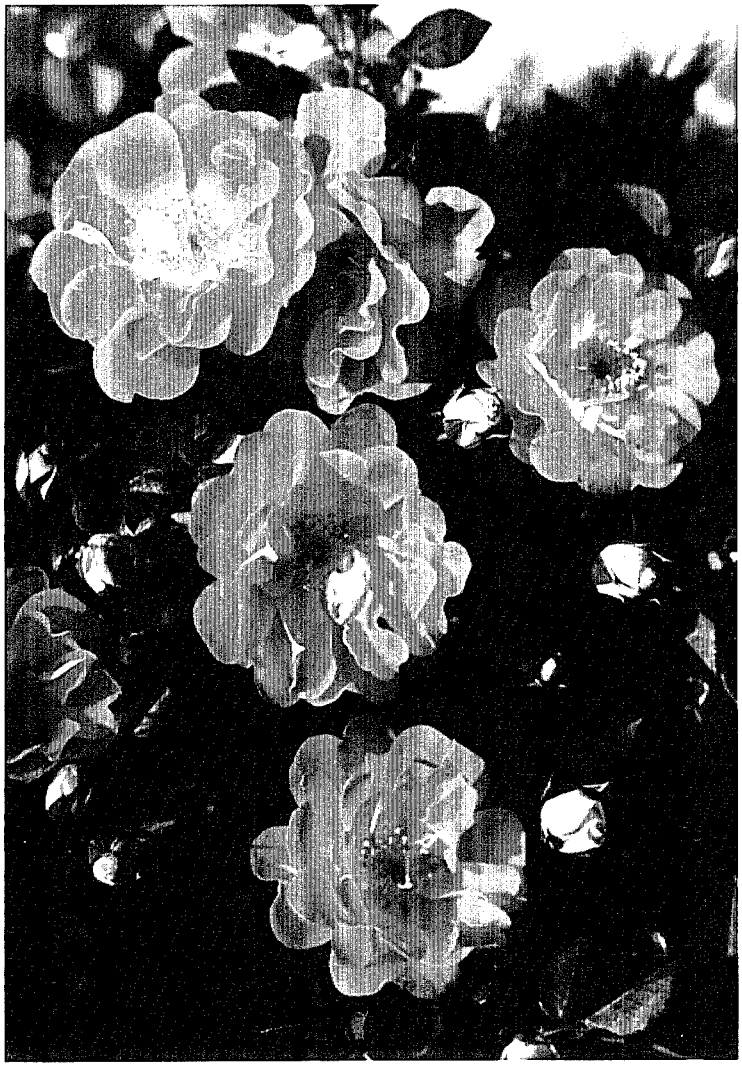

* * * * *